United States Patent
Paltieli et al.

(10) Patent No.: US 6,790,625 B1
(45) Date of Patent: Sep. 14, 2004

(54) ANTIBODIES TO PLACENTAL PROTEIN 13

(75) Inventors: Yoav Paltieli, Haifa (IL); Lev Rabinovitch, Kiryat Ata (IL)

(73) Assignee: Diagnostic Technologies Ltd., Haifa (IL)

( * ) Notice: Subject to any disclaimer, the term of this patent is extended or adjusted under 35 U.S.C. 154(b) by 0 days.

(21) Appl. No.: 09/937,706

(22) PCT Filed: Mar. 29, 2000

(86) PCT No.: PCT/IL00/00196

§ 371 (c)(1),
(2), (4) Date: Feb. 21, 2002

(87) PCT Pub. No.: WO00/58364

PCT Pub. Date: Oct. 5, 2000

(30) Foreign Application Priority Data

Mar. 30, 1999 (IL) ................................................. 129273

(51) Int. Cl.[7] ........................................... G01N 33/543
(52) U.S. Cl. ...................... 435/7.1; 435/7.5; 435/7.94; 435/975; 436/518; 436/547; 436/548; 530/380; 530/388.1; 530/388.15
(58) Field of Search ..................... 435/7.1, 7.5, 7.94, 435/975; 436/514, 518, 547, 548; 530/380, 388.1, 388.15

(56) References Cited

U.S. PATENT DOCUMENTS

| 4,500,451 A | 2/1985 | Bohn et al. |
| 5,198,366 A | 3/1993 | Silberman |
| 6,548,306 B1 * | 4/2003 | Admon et al. |

FOREIGN PATENT DOCUMENTS

| EP | 0 283 606 A1 | 9/1988 |
| WO | WO 99/38970 A1 | 8/1999 |

OTHER PUBLICATIONS

XP–000915077: Than et al., "Isolation and Sequence Analysis of a cDNA Encoding Human Placental Tissue Protein 13 (PP13), a New Lysophospholipase, Homologue of Human Eosinophil Charcot–Leyden Crystal Protein", *Placente*, (1999), 20(8), pp. 703–710.

* cited by examiner

Primary Examiner—Bao-Thuy L. Nguyen
(74) Attorney, Agent, or Firm—Browdy and Neimark, PLLC

(57) ABSTRACT

A monoclonal antibody (Mab) capable of binding Placental Protein 13 (pp-13) is disclosed. Also disclosed are hybridoma clone producing the Mab, an immunoassay using the Mab for measuring the level of PP-13 in a biological fluid, and a kit for measuring the level of PP-13 in a biological fluid.

17 Claims, 18 Drawing Sheets

SDS-PAGE ELECTROPHORESIS
OF MOUSE ANTI-PP-13 ASCITES & IgG

1. MW markers
2. Ascitic fluid #215-28-3
3. Purified IgG #215-28-3
4. Ascitic fluid #27-2-3
5. Purified IgG #27-2-3
6. Control (sample buffer)

SDS-PAGE ELECTROPHORESIS OF MOUSE ANTI-PP-13 ASCITES & IgG

1. MW markers
2. Ascitic fluid #215-28-3
3. Purified IgG #215-28-3
4. Ascitic fluid #27-2-3
5. Purified IgG #27-2-3
6. Control (sample buffer)

ANTIBODIES TO PLACENTAL PROTEIN 13

REFERENCE TO RELATED APPLICATIONS

The present application is the national stage under 35 U.S.C. 371 of international application PCT/I100/00196, filed Mar. 29, 2000 which designated the United States, and which international application was published under PCT Article 21(2) in the English language.

FIELD OF THE INVENTION

This invention relates to antibodies raised against a placental protein.

BACKGROUND OF THE INVENTION

References referred to in the text by a number enclosed by parenthesis are listed at the end of the specification.

The goal of pregnancy management is the delivery of a mature, healthy infant, without encountering complications which can adversely affect the well being of both the mother and the newborn. A significant percentage of pregnancies are affected by various disorders. Among them are preterm delivery, intrauterine growth retardation and preeclampsia. These complications negatively impact the outcome of affected pregnancies, at enormous cost both to the patients as well as to the health system.

Placental Protein 13 (PP13) is a protein which was previously isolated from human placental tissue (U.S. Pat. No. 4,500,451 to Bohn, et al., the contents of which are incorporated herein by reference). The protein was characterized by the following parameters: electrophoretic mobility, isoelectric point, sedimentation coefficient, molecular weight determined by ultracentrifugation molecular weight determined by SDS-PAGE electrophoresis, extinction coefficient and carbohydrate content. The amino acid composition (residues per 100 residues) was determined but not the amino acid sequence.

PP13 was used to develop an assay for the early stage detection of three specific pregnancy-related disorders: intrauterine growth retardation, preeclampsia and preterm deliver (U.S. Pat. No. 5,198,366 to Silberman, the contents of which are incorporated herein by reference). Both a radioimmunoassay (RIA) and an enzyme-linked immunosorbent assay (ELISA) were developed using labeled PP13 and anti PP13 polyclonal antiserum, respectively. However, experimental results were given only for the RIA, and not for the ELISA. No further properties of PP13 are disclosed in the Silberman patent. There have also been reports in the literature regarding the determination of other placental proteins and their relationship to pregnancy disorders (1–3).

The ELISA fulfils requirements of objectivity, simplicity, sensitivity and specificity previously only attained by radioimmunoassay (4). A methodological comparison of ELISA and RIA reveals several advantages of the former method:

1. ELISA is absolutely safe and does not require a specially designed laboratory and trained personnel for working with radioactive material.
2. Two-antibody sandwich ELISA is a more sensitive, rapid and easily quantitatable method.
3. Enzymes are rather stable as compared with radioactive tracers and cause a high level of result reproducibility.
4. The enzymatic activity may be measured easily using the spectrophotometric principle of an ELISA-reader, which is much cheaper and simpler in handling than a gamma-counter.
5. ELISA is more suitable for automation.

It is therefore desirable to develop an improved ELISA for the determination of PP13 levels.

SUMMARY OF THE INVENTION

It is an object of the present invention to provide monoclonal antibodies (Mab) capable of binding PP13.

It is a further object of the invention to provide an immunoassay which measures the level of PP13 in biological fluids.

In one aspect of the invention, there is provided a Mab capable of binding PP13. In particular, the invention provides hybridoma clones selected from the group consisting of clones #26-2, 27-2-3, 215-28-3, 534-16 and 606-8-11-67, as well as the Mab produced by these clones. These clones have been deposited in accordance with the Budapest Treaty at the Collection Nationale de Cultures de Microorganismes of the Pasteur Institute of 25, Rue du Docteur Roux, Paris, France. The following are the depository details of the clones:

| Clone # | Accession No. | Deposit Date |
| --- | --- | --- |
| 26-2 | I-2134 | Mar. 4, 1999 |
| 27-2-3 | I-2135 | Mar. 4, 1999 |
| 215-28-3 | I-2136 | Mar. 4, 1999 |
| 534-16 | I-2137 | Mar. 4, 1999 |
| 606-8-11-67 | I-2138 | Mar. 4, 1999 |

In another aspect of the invention, there is provided an immunoassay for measuring the level of PP-13 in a biological fluid comprising the steps of: (a) bringing the fluid into contact with a Mab according to the invention, thereby forming Mab-PP-13 complexes; (b) exposing the complexes to a second antibody linked to a signal-generating molecule, the second antibody being capable of binding the complexes; and (c) providing conditions conducive to the production of a signal generated by the signal-generating molecule.

In the present specification, the term "signal-generating molecule" relates to a molecule capable of generating, either directly or indirectly, a detectable signal. The signal may be, e.g. a radioactive emission or a spectrophotometric absorbance at a specific wavelength. Preferably, the signal will be a color which can be detected by a spectrophotometric reader. The signal-generating molecule may generate the signal directly, e.g. by reacting itself with a chromogenic substrate, or indirectly, e.g. by binding to another molecule which is able to generate a signal. In a preferred embodiment, the signal-generating molecule is a ligand which generates a signal indirectly by binding to a ligand-binding molecule which is linked to an enzyme, which in turn catalyzes a reaction resulting in color formation.

The biological fluid may be any fluid which may contain PP13, such as placental extract or blood serum. Preferably, the fluid is blood serum. In one embodiment of this aspect of the invention, the Mab, which binds one site on PP13, is bound to a solid phase such as a microtiter well or a bead. The second antibody will be capable of binding another site on PP13, and may be polyclonal or monoclonal. In a preferred embodiment, the second antibody is also a Mab according to the invention.

In a further aspect of the invention, there is provided a kit for measuring the level of PP-13 in a biological fluid comprising: (a) a Mab according to the invention; (b) a second antibody linked to a signal-generating molecule; and (c) PP-13 standard solutions. In a preferred embodiment, the second antibody is also a Mab, as described above. The kit may be used to carry out an immunoassay as described above.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF PREFERRED EMBODIMENTS

Figure 1:
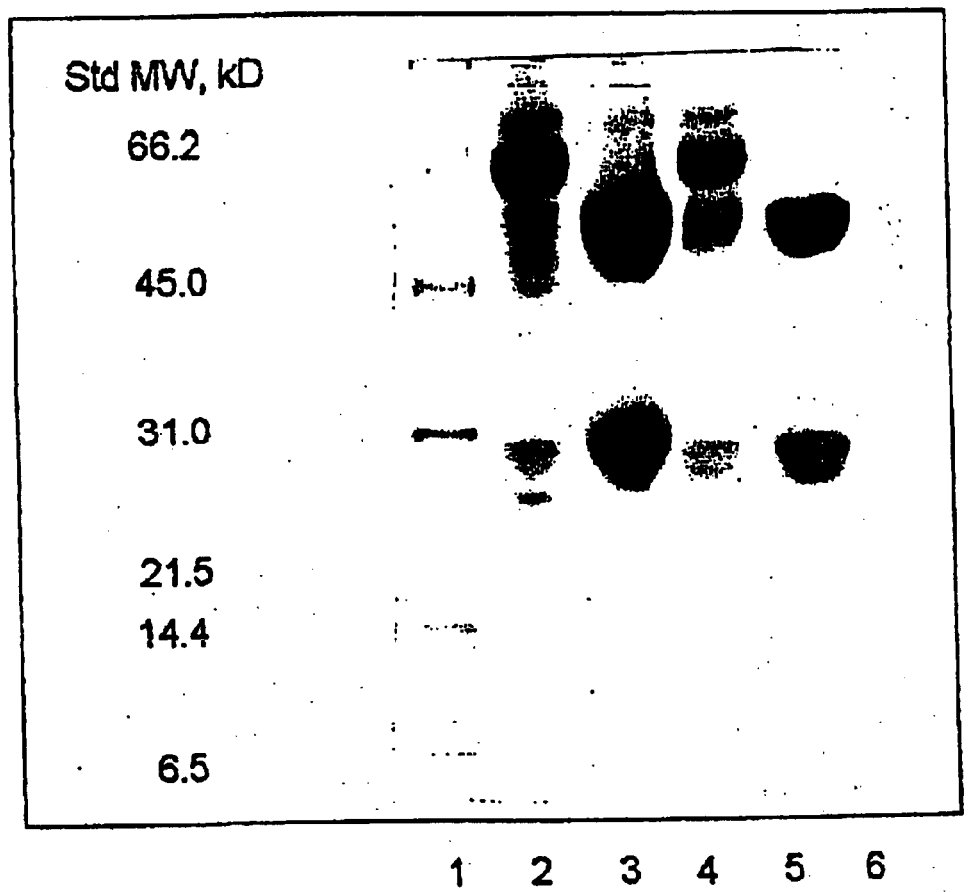
FIG. 1 shows a SDS-PAGE electrophoresis of mouse anti-PP-13 ascites & IgG (the gel is overloaded for visualization of impurities)

Materials and Methods
(a) Purification of PP-13

PP-13 used in this study was isolated and purified from human placenta according to the method described by Bohn et al. with some modifications. Freshly obtained placenta was stripped of membranes and the maternal outer layer. The inner fetal trophoblast region was chopped into small pieces and homogenized in a blender with about 1.5 liters of DDW for 5 min. All subsequent steps were carried out at 40° C. The pH of the extract was adjusted to 7.0 by adding several drops of concentrated NaOH. The extract was then rehomogenized with a tissue homogenizer (Politron) for 5 min. in batches of 300 ml. The homogenized placental extract wag stirred for 30 min. and then centrifuged for 60 min. at 10,000 rpm (Sorval large rotor). The supernatant was saved, supplemented with 0.5M NaCl. 100 mM Tris-HCl, 0.05% Tween 20 and 0.1% $NaN_3$, and filtered through depth filters, using a vacuum pump. The filtrate containing PP-13 was collected for the first immunoabsorbance column and stored at −20° C.

A 60 ml bed volume anti-PP-13 immunoabsorbance column (I), containing rabbit anti-PP-13 IgG fraction was equilibrated with buffer A (1M NaCl, 100 mM Tris-HCl, 0.1% $NaN_3$, pH 8.0). This column was sufficient to handle the extract of one placenta. The placental extract was loaded onto the column at a flow rate of 4 ml/min. The column was washed with buffer A until the optical density (OD) level reached the baseline. The PP-13 peak was eluted from the column with a 6 M urea solution (treated with 1 mg/10 ml of amberlite ionic exchanger MB-6, 20–50 mesh). The eluted protein solution (about 150 ml) was concentrated by ultrafiltration, using 10 kD MW cut-off disk membranes, to a final volume of 50 ml. At the same time, the buffer was switched to phosphate buffer saline (PBS), containing 0.1% $NaN_3$, pH 7.4.

A 60 ml bed volume anti-placental extract negative immunoabsorbance column (II), containing rabbit anti-human placental extract IgG fraction was equilibrated with PBS+ 0.1% $NaN_3$, pH 7.4. PP-13 enriched extract obtained from column I was loaded onto the column at a flow rate of 3 ml/min. The unbound protein (about 130 ml) was collected and concentrated using 10 kD MW cut-off disk membranes to a final volume of 40 ml. The column was regenerated with 6M urea solution to remove impurities bound to the column and washed with 5 bed volumes of PBS+0.1% sodium azide.

A 56 ml bed volume anti-human globulin negative immunoabsorbance column (III), containing rabbit anti-human alfa-1, beta -and delta-globulins IgG was equilibrated with PBS. The PP-13 concentrated extract obtained from the column II was loaded onto the column III at a flow rate of 3 ml/min. Unbound protein (about 120 ml) was collected and the column was regenerated with 6M urea solution and washed with PBS. This material was repurified using the first immunoabsorbance column, and then used for gel-filtration chromatography which was performed on a Superdex 75 Hiload 26/60 column. The concentrated PP-13 fraction (about 3 ml) was loaded onto the gel-filtration column equilibrated previously with PBS at a flow rate of 3 ml/min. The column was washed with PBS and fractions of 5 ml each were collected. PP-13 was eluted as a third peak, concentrated to a volume of 1 ml. analyzed for purity by SDS-PAGE electrophoresis (5) and quantitated by the Microbradford method and by ELISA.

(b) Development of Anti-PP-13 Monoclonal Antibodies

Monoclonal anti-PP-13 antibodies (Mab) were produced in the Weizmann Institute (Israel). Five three-month old female Balb/c mice (Jackson) were immunized twice with 0.05 mg PP-13 in PBS and complete Freund's adjuvant per injection per mouse (i.d. and s.c.), and twice with PP-13 in PBS without adjuvant. The injections were made into each of the hind-footpads and afterwards at multiple sites at both the sides and back of the mice. The injections were separated by an interval of two weeks. Test bleeds were carried out 10 days after the third and fourth immunizations.

Three weeks later, two mice having the best response (see results section) received two injections of 0.05 mg PP-13 i.p. during two consecutive days. Five days after the last boost, spleens of those two mice were removed and 100 million cells from each individual spleen were fused using 41% polyethylene glycol 1500 (Serva. Heidelberg, FRG) with 20 million NSO/1 myeloma line cells kindly provided by C. Milstein (MRC, Cambridge, UK), as described previously (6).

Following fusion, cells were distributed into six microplates (96 wells each) at a concentration of 50,000 viable cells/well. Hybrid cells selected for growth in the presence of HAT were kept in a humidified incubator in the presence of 8% $CO_2$ in air. The growth medium was Dulbecco's modified Eagle's medium (DMEM high glucose, Gibco) supplemented with 1 mM pyruvate, 2 mM glutamine, penicillin (10 units/ml), streptomycin (0.02 mg/ml) and 15% heat inactivated horse serum (HS, Beit Haemek Biological Industries, Israel). Positive hybrid cultures were weaned out of HAT, cloned by limiting dilution, recloned in soft agar and propagated in vitro in large volumes of DMEM-HS or in vivo as ascites in pyrstane-treated (BALB/c×DBA/2) mice.

Ascitic fluids produced using the best clones were affinity purified on a protein G column (Sigma, Cat. #P 4691). IgG fractions were collected, dialyzed, concentrated, quantitated and tested in an antibody-capture direct ELISA. Aliquots were biotinylated and tested again in an antibody-capture direct ELISA and in variants of a two-monoclonal Ab sandwich ELISA. The best combination of antibodies with the highest sensitivity was chosen for development of a two-monoclonal Ab sandwich ELISA.

Antibody-capture direct ELISA was employed for the screening of anti-PP-13 antibodies. Microtiter plates were coated with purified PP-13 and blocked with 1% BSA in PBS. Antisera of test bleeds, hybridoma culture supernatants or ascitic fluids were applied as a primary antibody. Normal mouse serum (NMS) served as a negative control. AP-goat anti-mouse IgG (Fc) without cross-reactivity with other mouse immunoglobulins (Sigma, Cat. #A 1418) and Biotin-goat anti-mouse IgM (Zymed Laboratories, Inc., Cat. #62-6840) were used as the secondary antibodies for determination of antibody class specificity. AP-Extravidin was applied to the microplate wells previously incubated with biotinylated Ab.

After incubation with the substrate, optical density was detected in a Microplate-reader (BIO-TEK Instruments. Inc.) at 405 nm. Since the affinity of the Ab is closely related to the sensitivity of an assay, monoclonal Ab affinities and ability to work with another Ab as a pair were evaluated using two-antibody sandwich ELISA with rabbit polyclonal anti-PP-13 IgG as a primary Ab. Purified PP-13 served as a standard solution with concentrations from 0 to 2.0 ng/ml. Antisera of test bleeds, hybridoma culture supernatants or ascitic fluids were applied as the secondary antibodies. AP-goat anti-mouse IgG was used as detecting Ab. After incubation with the substrate, ELISA plates were scanned in the Microplate-reader at 405 nm.

(c) Two-monoclonal Antibody Sandwich ELISA

A two-monoclonal antibody sandwich solid-phase enzyme immunoassay with biotin-extravidin amplification system was established for PP-13 measurement in biological fluids. Highly purified PP-13 from human placenta was used as a standard and control. Two IgG fractions of purified ascitic fluids showed the best result in the two-antibody sandwich assay test used for ELISA development. The level of their purity was controlled by SDS-PAGE electrophoresis (FIG. 1). One Ab was used for coating of flat bottom 96-well Nunc-microplates while the second served as a secondary antibody after biotinylation.

ELISA plates were coated with anti-PP-13 IgG in PBS and incubated for 2 hours at room temperature. After incubation the plates were washed 3 times with PBS+0.05% Tween 20 and blocked with assay buffer (PBS+1% BSA+ 0.05% Tween 20) for 2 hours at room temperature. Afterwards the plates were washed in the same manner, PP-13 standard and controls diluted in pooled male serum/assay buffer (1:3) or unknown specimen (blood serum) diluted in assay buffer (1:3) were loaded and microplates were incubated overnight at room temperature. After this and all the following steps the plates were washed 3 times with assay buffer. Biotin-anti-PP-13 IgG in assay buffer as a secondary Ab was added and the plates were incubated for 2 hours at room temperature. Then ELISA plates were incubated with extravidin-alkaline phosphatase solution (Sigma, Cat. #E 2636) in assay buffer for 2 hours at room temperature. The reaction was developed by adding substrate-chromogen mixture (Sigma, Cat. #104–105) and the results were detected by an ELISA reader at 405 nm. The amount of standard or unknown antigen was determined as an optical density (OD) of the sample minus blank (pooled male serum/assay buffer, 1:3). A standard curve was established by plotting this data against the known amount of PP-13. 2SD confidence interval of standard curve has been plotted as a basis for the quality control statistics. Results were calculated using Dbase software.

Results (a) Testing of Anti-PP-13 Monoclonal Antibodies (i) Test Bleeds

Figure 2:
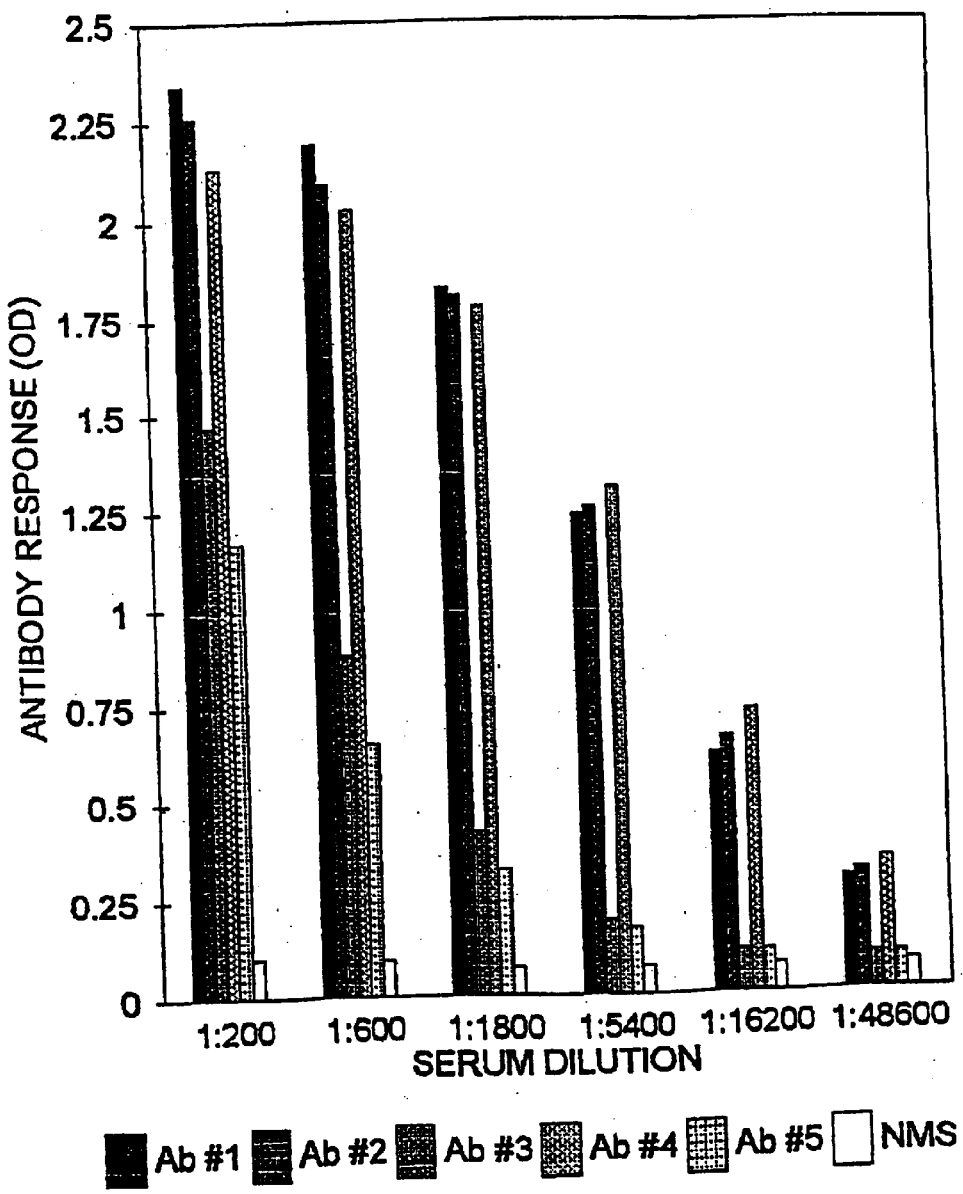
FIG. 2 illustrates testing of mouse anti-PP-13 serum in a direct ELISA.

Blood sera obtained from five immunized mice during test bleeds were titered (1:200–1:48600) to monitor the development of the response. Blood samples were checked in antibody capture direct ELISA. Mice #1, 2, 4 were found to have a strong response: high levels of specific Ab were detected. Titers of antisera from mice #3 and #5 were lower (FIG. 2). The same mice showed quite high antibody affinities in sandwich ELISA recognizing different concentrations of PP-13 starting from 50 pg/ml (not shown). Two mice, #1 and #2 having the best response, were chosen for the last boost and fusion.

(ii) Screening of Tissue Culture Supernatnats (Sups)

Figure 3:
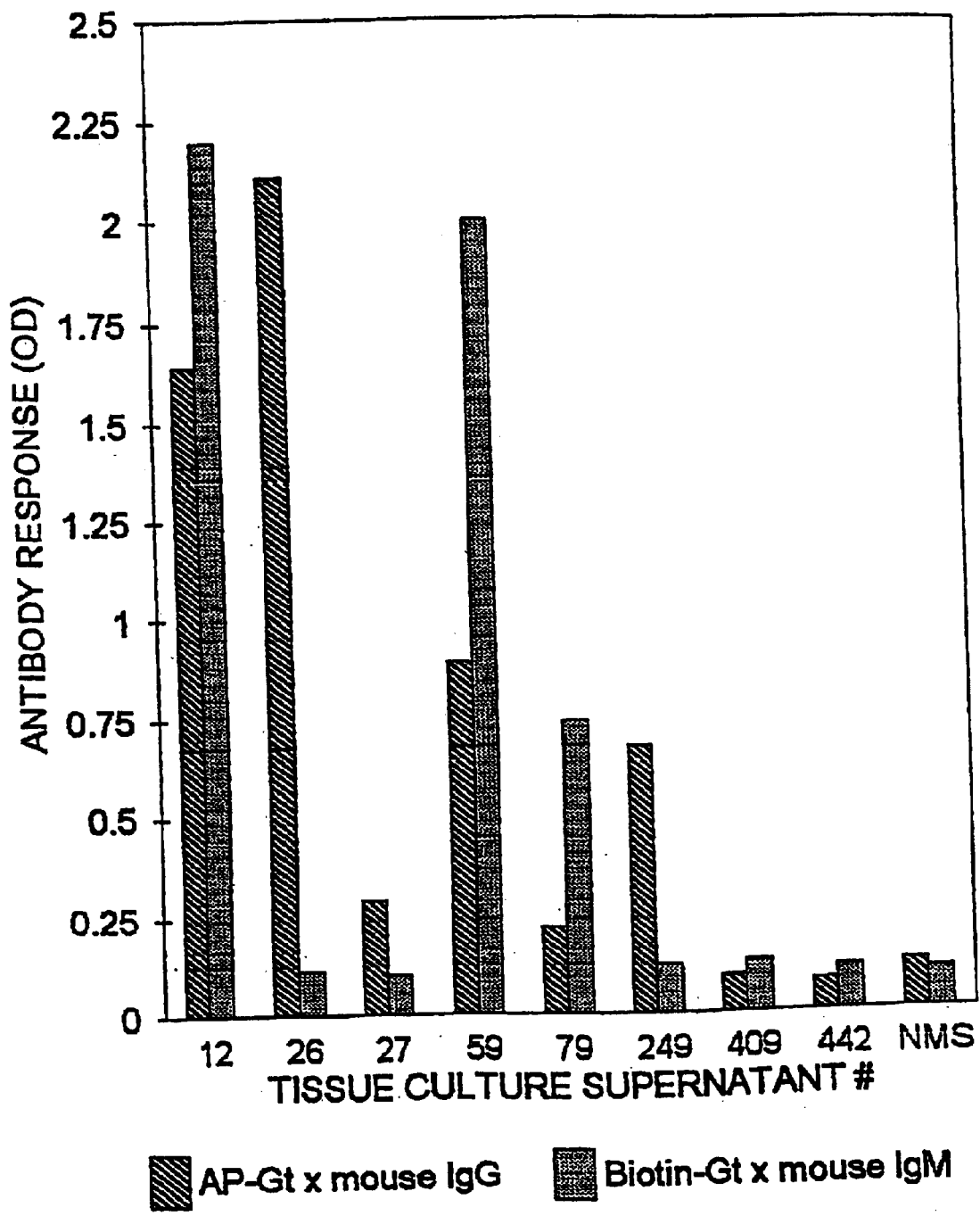
FIG. 3 illustrates classing of anti-PP-13 antibodies in a direct ELISA.

Tissue culture sups were screened periodically during hybridoma growing by antibody capture ELISA using AP-goat anti-mouse IgG. Positive samples were rescreened using the same secondary Ab and Biotin-goat anti-mouse IgM for identifying the class of Ab. Sups #12, 26, 27, 59, 79, 140, 215, 249, 409, 442, 489, 502, 531, 534, 606, 669, 676, 808, 882 were rescreened. It was found, that Ab #26, 27, 215, 249, 534, 606, 669, 882 belonged to IgG class, Ab #12, 59, 79, 489, 502, 531, 676 were classified as IgM and Ab #140, 409, 442, 808 showed low levels with both secondary Abs (selected results are shown in FIG. 3).

Figure 4:
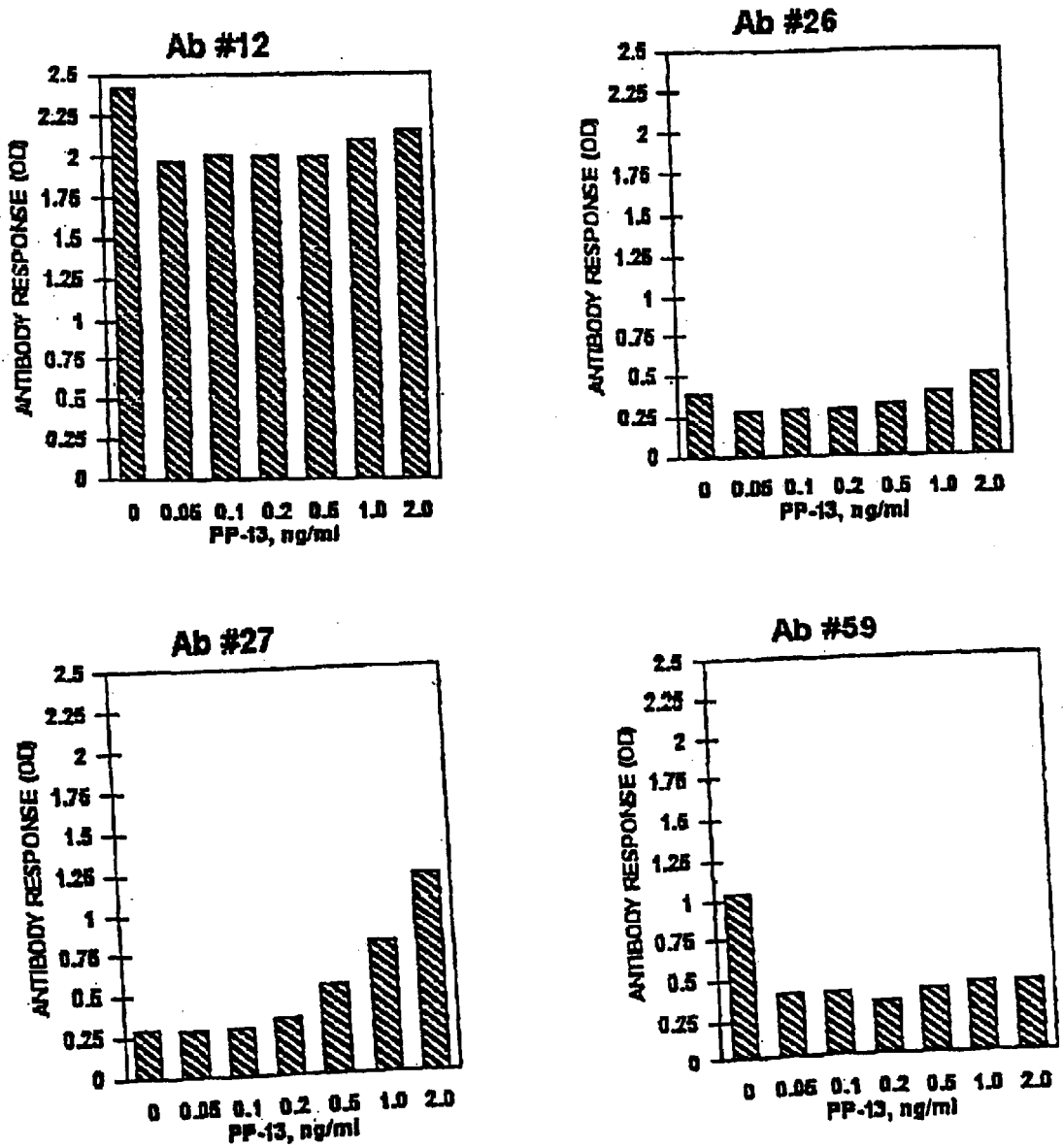
FIGS. 4 & 5 illustrate testing of anti-PP-13 antibodies in a sandwich ELISA.
Figure 4:
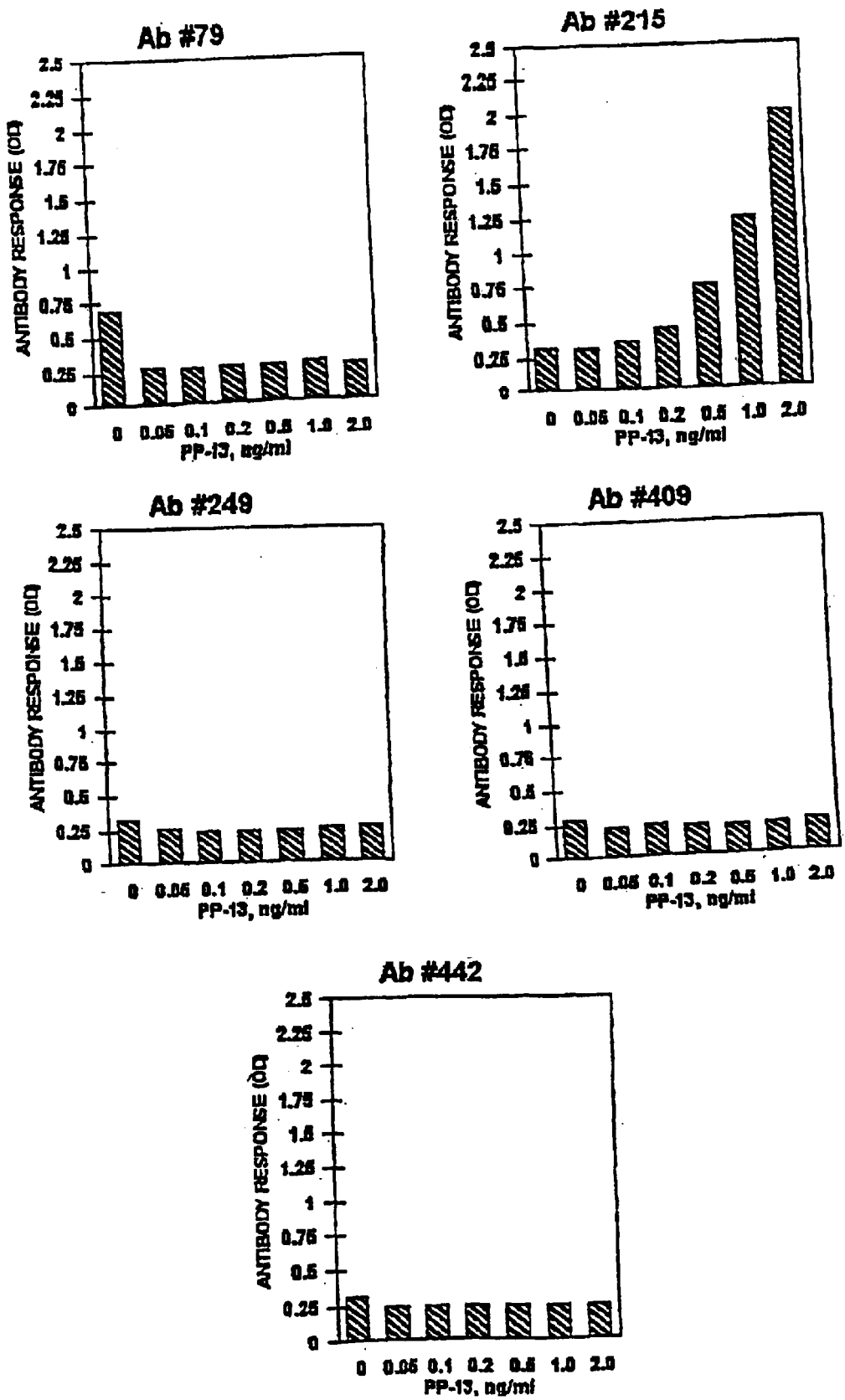
Figure 5:
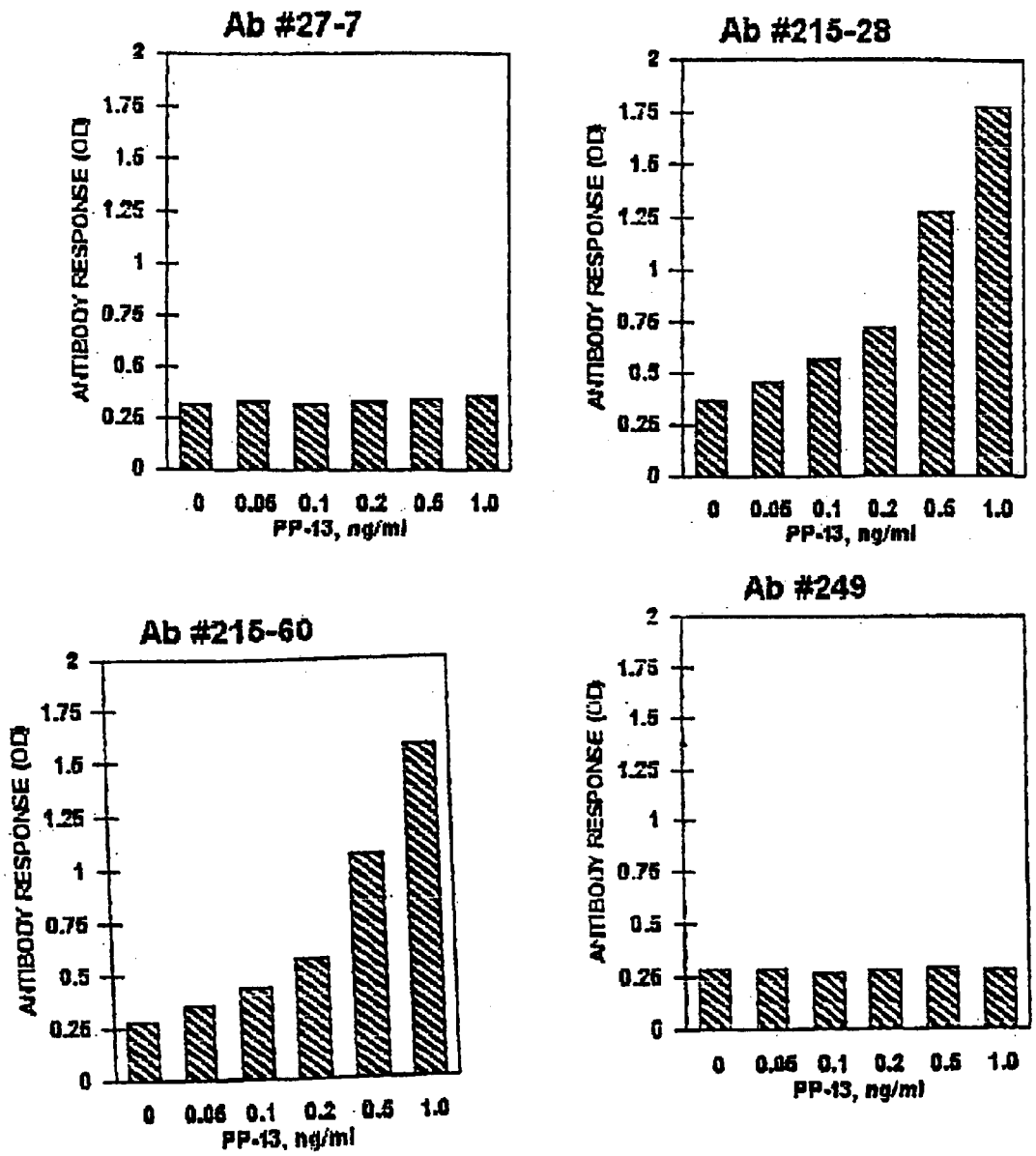
Figure 5:
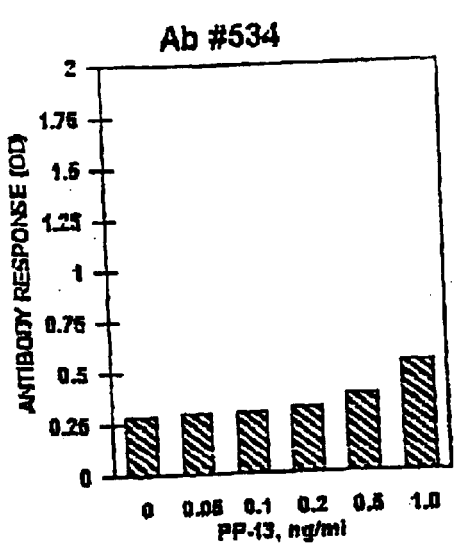
Figure 5:
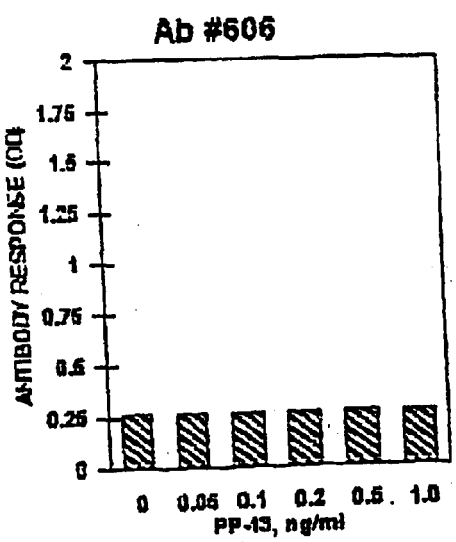
Figure 5:
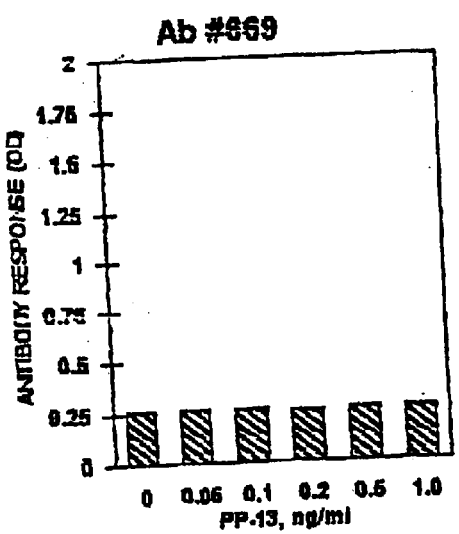
Figure 5:
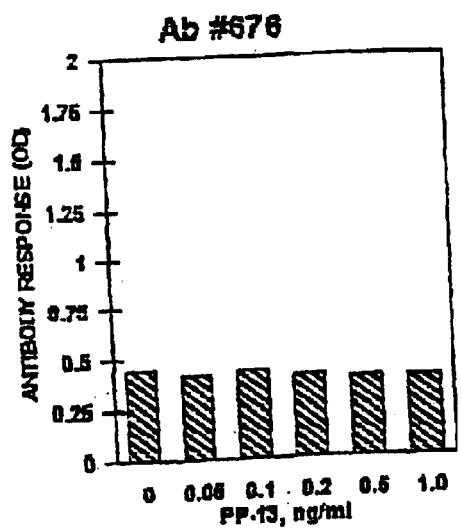
Figure 5:
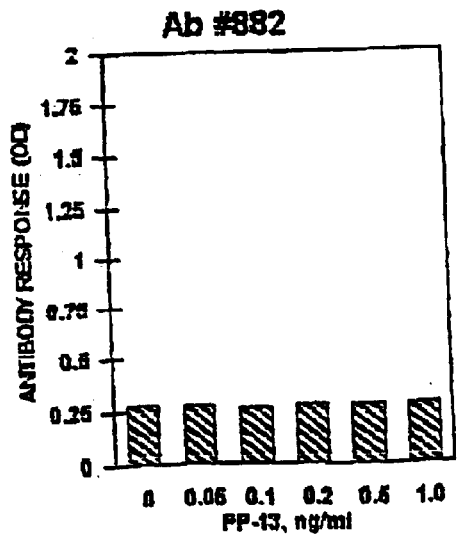
Figure 6:
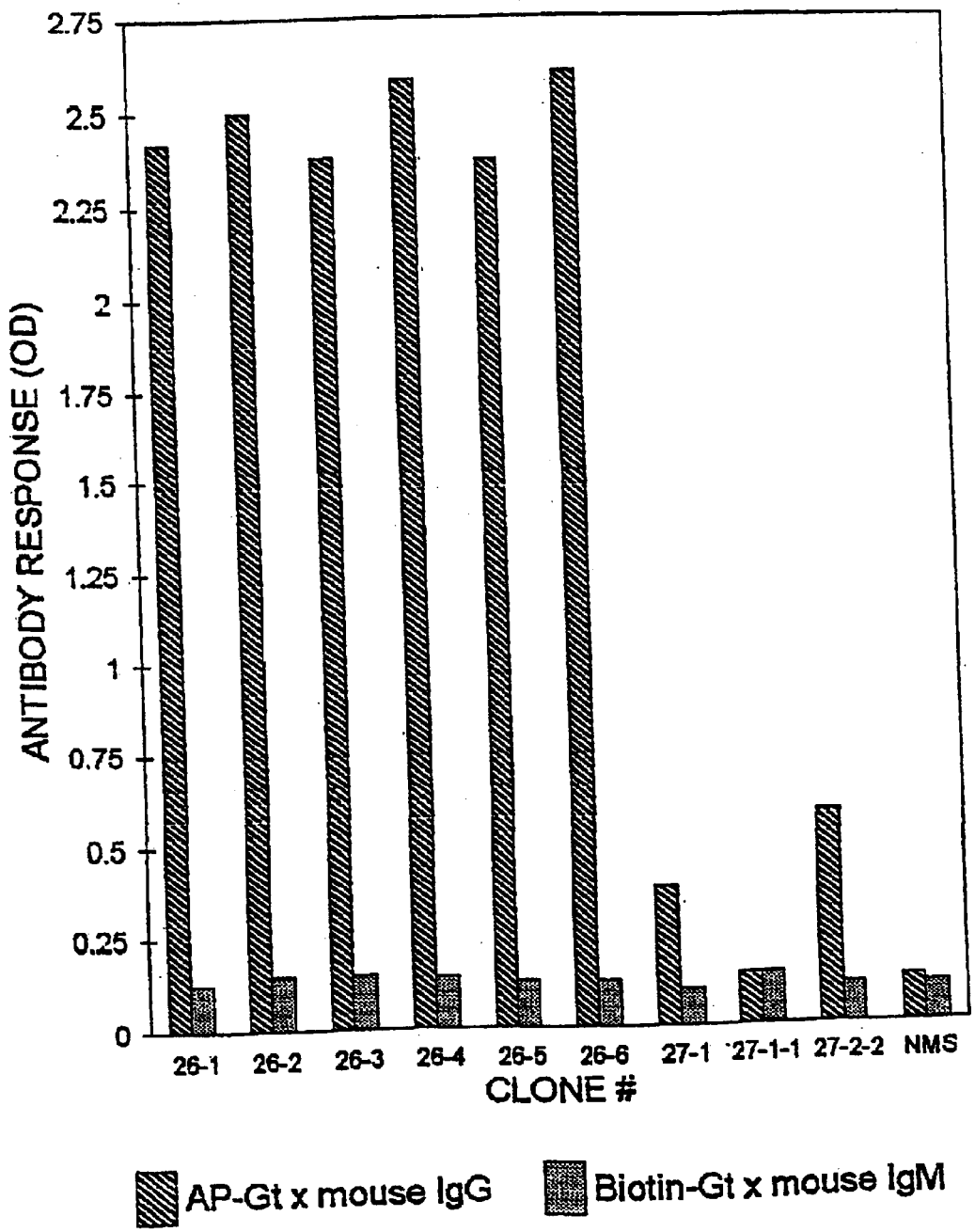
FIGS. 6–9 illustrate classing of anti-PP-13 antibodies in a direct ELISA (cloning: $2^{nd}$ screening)
Figure 7:
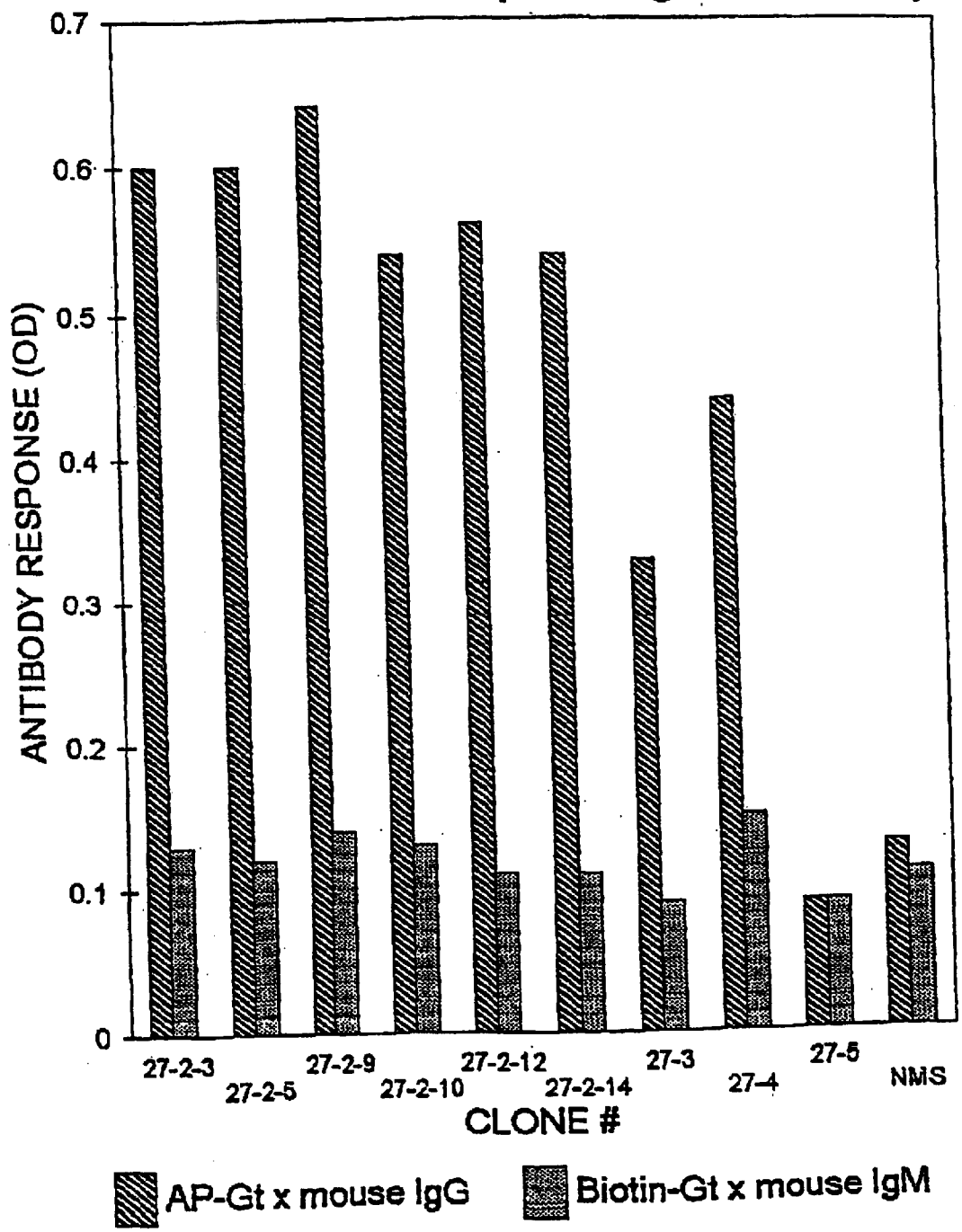
Figure 8:
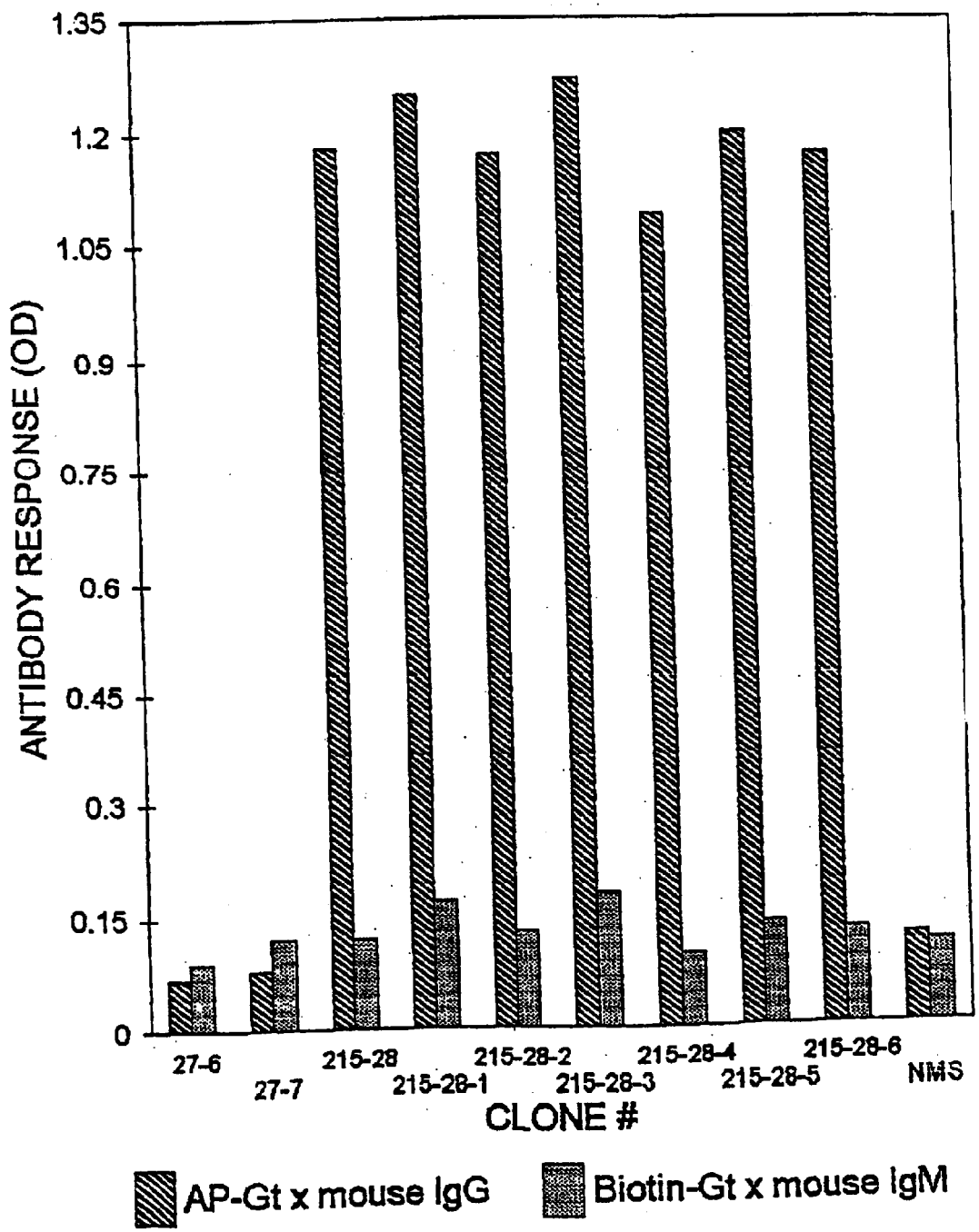
Figure 9:
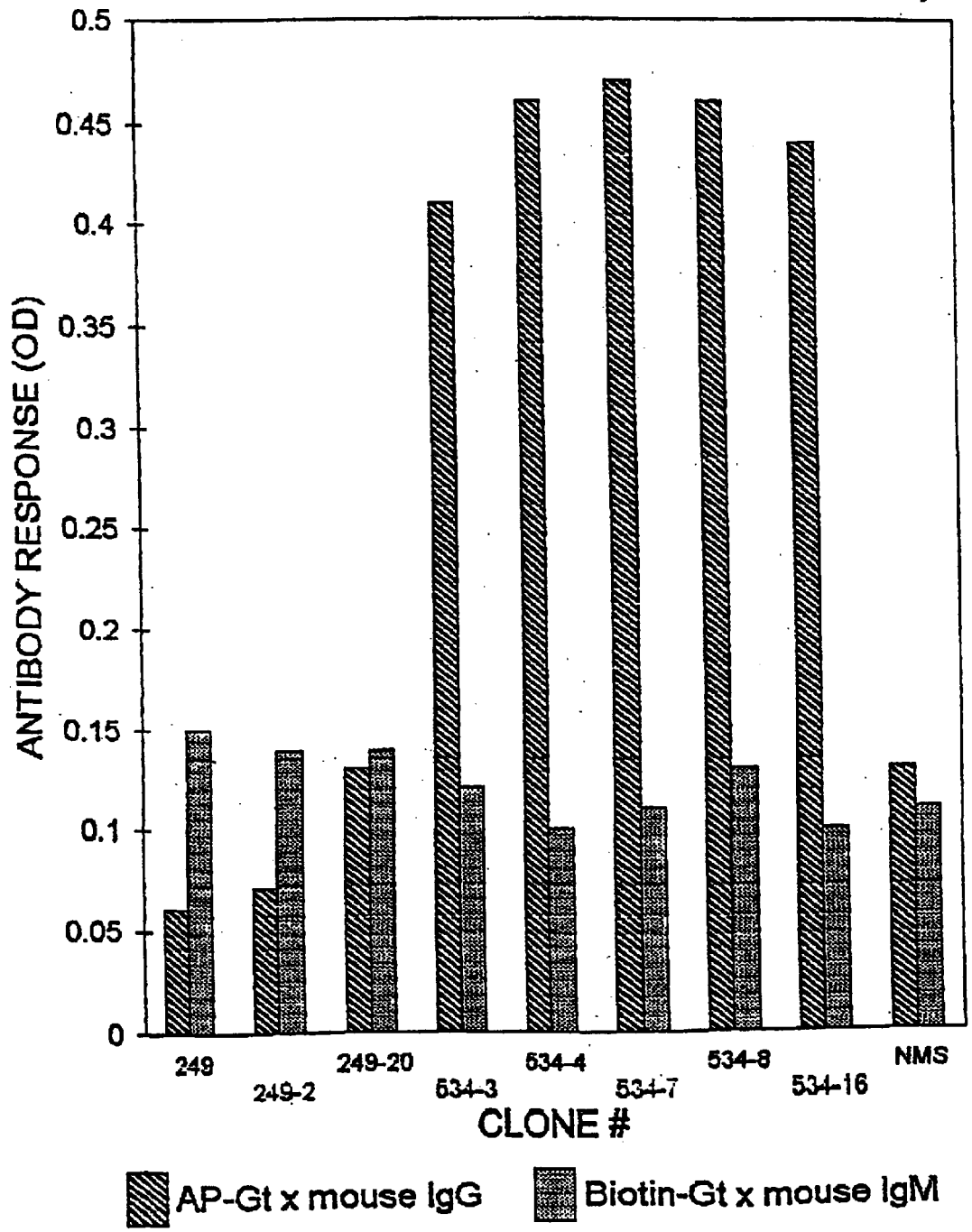
Figure 10:
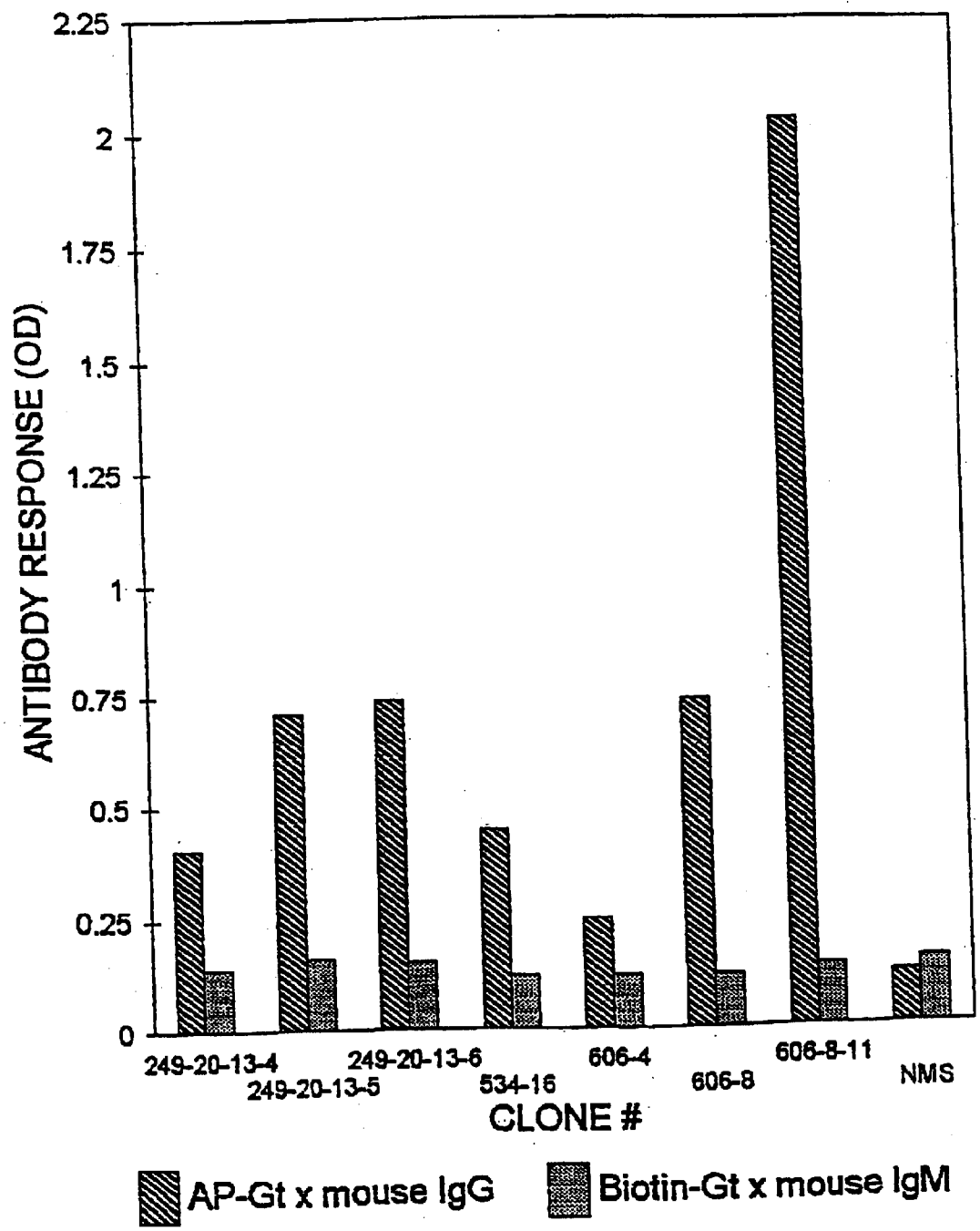
FIG. 10 illustrates classing of anti-PP-13 antibodies in a direct ELISA (cloning: $3^{rd}$ screening)

The Ab affinities were evaluated in sandwich ELISA with rabbit anti-PP-13 IgG as a primary Ab. Tissue cultures #27, 215 and 534 produced Ab with high affinity (selected results are shown in FIG. 4). Tissue cultures #26, 27, 215, 249, 534, 606, 669, 882 producing Ab of IgG class were chosen for cloning. Their clones were rescreened in the same manner (FIGS. 5–10). Taking into consideration the class, level and affinity of Ab, the most stable clones #26-2, 27-2-3, 215-28-3, 534-16, 606-8-11-67 were used for the induction of ascites:

Clone #26-2 produced Ab of IgG class with a high level of response.

Clone #27-2-3 produced Ab of IgG class with high affinity; the detection limit was 0.05 ng/ml of PP-13.

Clone #215-28-3 produced Ab of IgG class with relatively high response and best affinity, recognizing different concentrations of PP-13 starting from 0.05 ng/ml.

Clone #534-16 produced Ab of IgG class with relatively high affinity: the detection limit of PP-13 concentration was 0.2 ng/ml.

Clone #606-8-11-67 produced Ab of IgG class with a high level of response.

(iii) Purifying and Testing Ascitic Fluids

Figure 11:
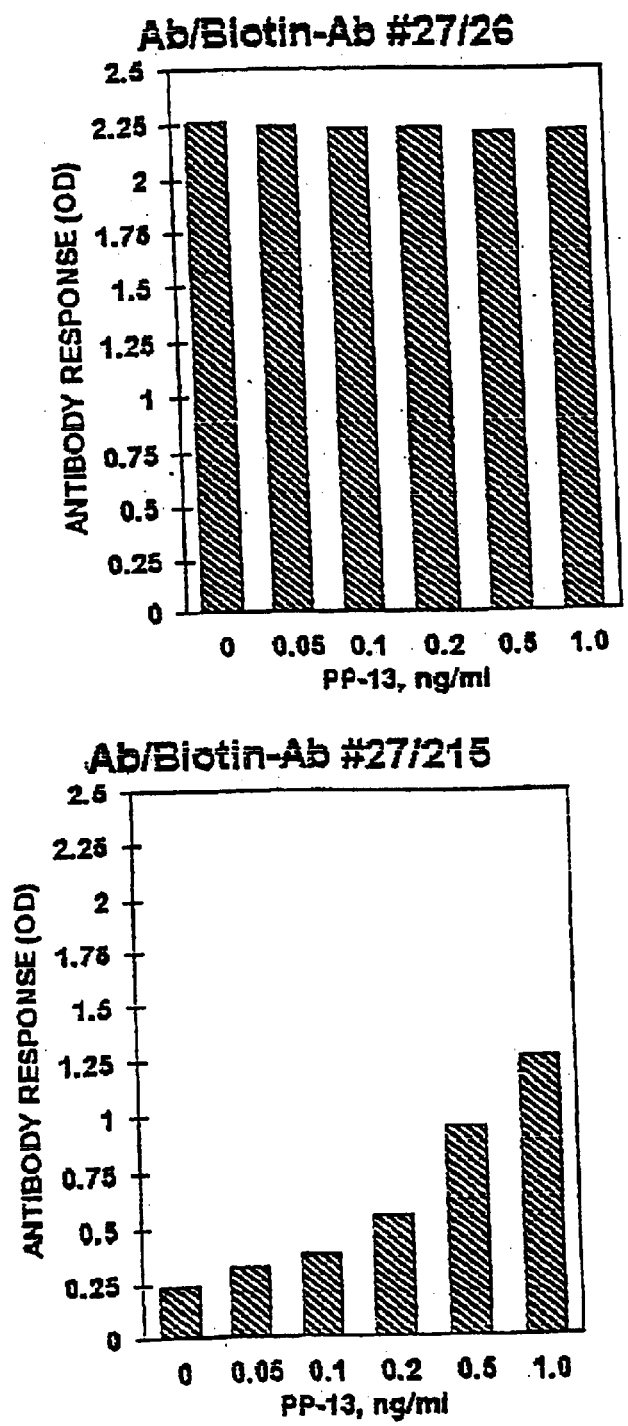
FIG. 11 illustrates a two-monoclonal antibody sandwich ELISA in different variants.
Figure 11:
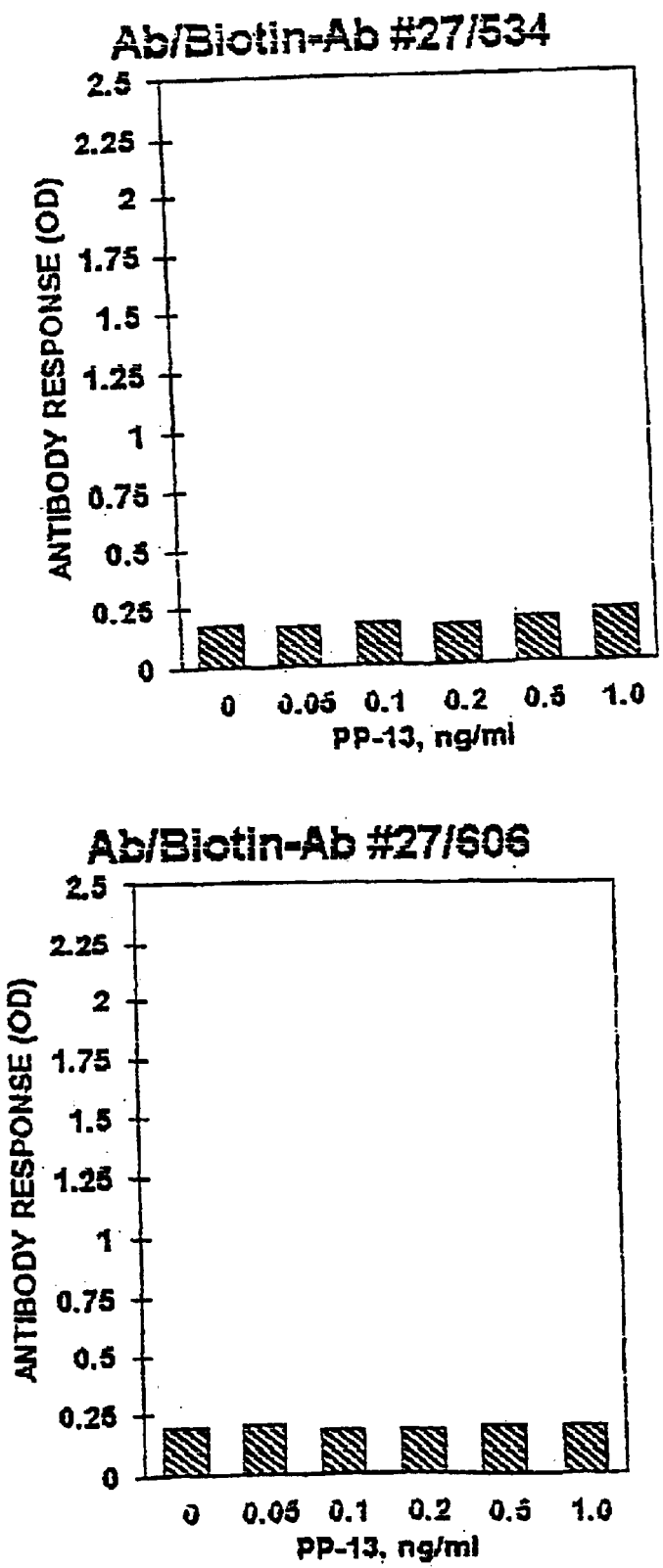

Five ascites #26-2, 27-2-3, 215-28-3, 534-16, 606-8-11-67 were affinity purified on a protein G column (Sigma, Cat. # P 4691). Their IgG fractions were tested in the Ab capture direct ELISA confirming IgG class. Aliquots of these Ab were biotinylated. After labeling, biotin-Ab were checked in the Ab capture direct ELISA, using AP-Extravidin as detecting reagent. All the Abs recognized PP-13 after biotinylation. Two-antibody sandwich assays with different combinations of primary and secondary Ab were carried out. The most effective variant was found to use IgG #27-2-3 for coating and Biotin-IgG #215-28-3 as a secondary Ab (FIG. 11). The sensitivity of this assay was 0.05 ng/ml of PP-13.

Figure 12:
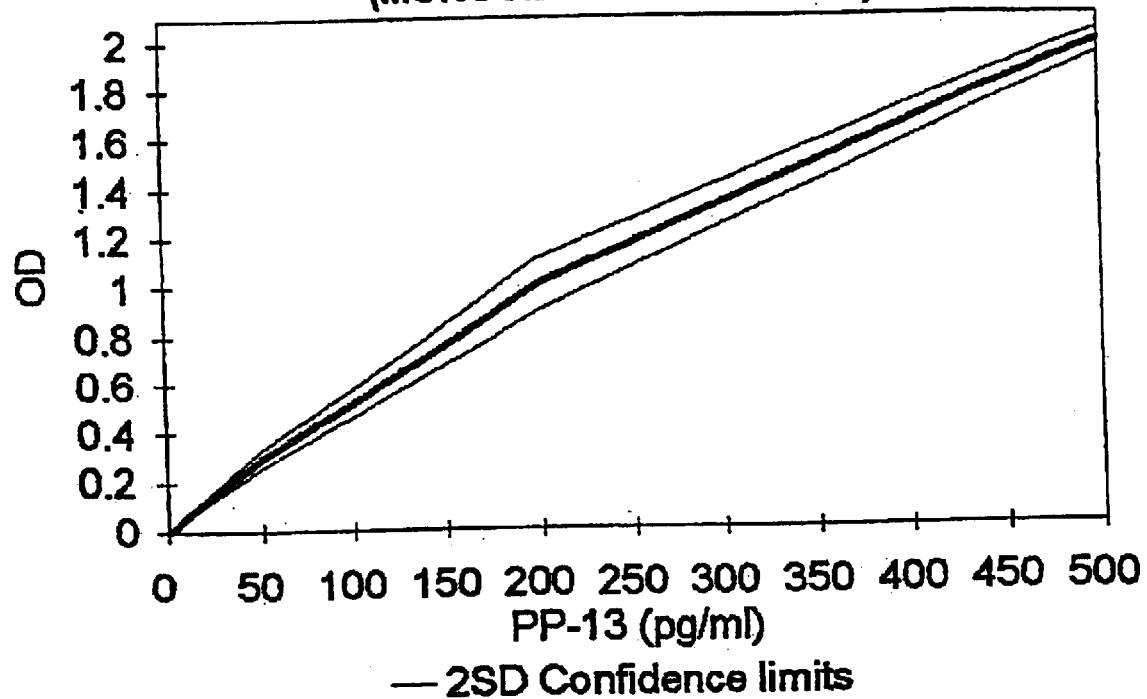
FIG. 12 shows a standard curve of PP-13 ELISA (monoclonal sandwich)

(b) Characterization of Two-antibody Sandwich ELISA (i) Standard Curve Statistics Assay conditions of a two-antibody sandwich ELISA were optimized and a standard curve was constructed. Different concentrations of PP-13 were used: 10, 20, 50, 100, 200, 500 pg/ml (FIG. 12). Optical densities of P-13 standard samples minus blank vs. known amount of PP-13 were plotted. An effective range of from 10 to 500 pg/ml PP-13 concentrations was reliably measured. The standard curve shape was nearly linear; the correlation coefficient between PP-13 concentrations and optical densities was r=0.99. The SD of residuals from the line=0.08, p value<0.0001 (two tailed). Its slope was quite steep, with a y-axis intercept near 0. Averaged coefficient of variation of standard curve data points was 5.6%, and 2SD confidence limits were rather narrow.

(ii) Sensitivity of the Test

Figure 13:
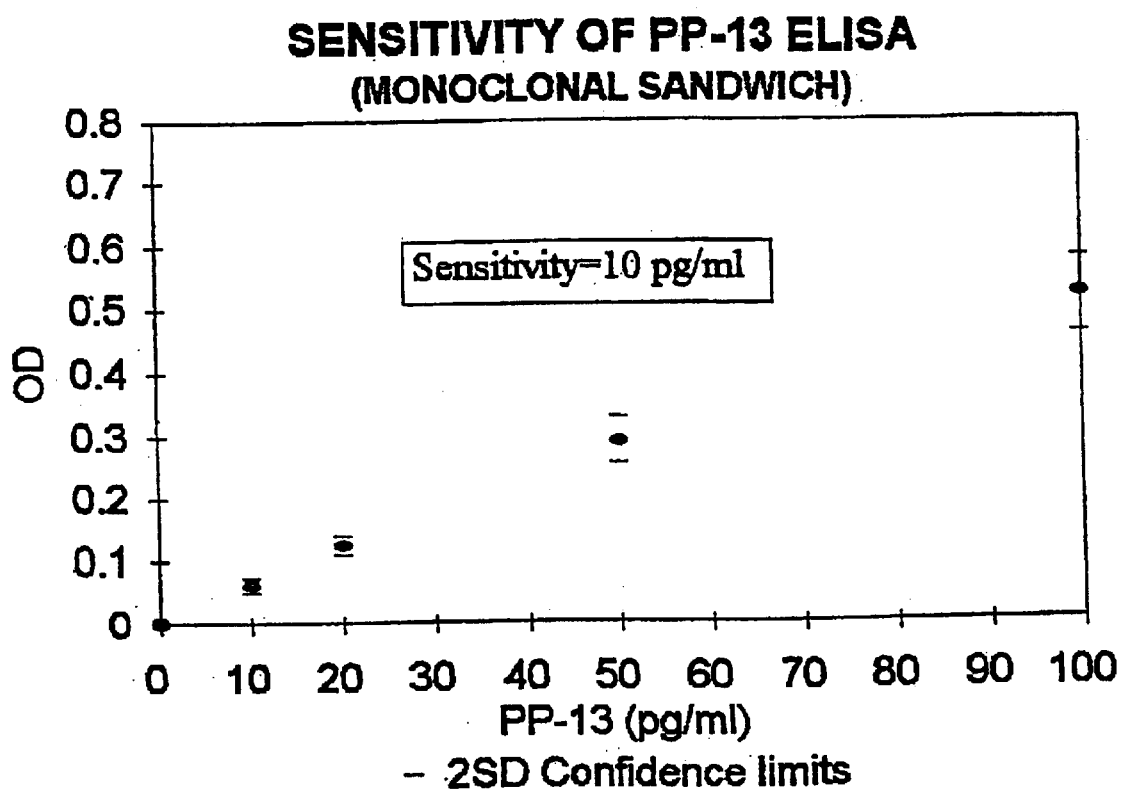
FIG. 13 illustrates sensitivity of PP-13 ELISA (monoclonal sandwich)

This parameter is defined as the minimal detection limit of an assay which is to be determined as the least concentration of PP-13 which can be distinguished from a sample containing no protein. The distinction is based on the confidence limits of the estimate of the zero standard on the one hand, and the standard on the other. It is seen from the graph (FIG. 13) that 10 pg/ml of PP-13 could be clearly distinguished from zero. This is the maximum sensitivity which can be attained using the sandwich ELISA technique.

(iii) Specificity

Figure 14:
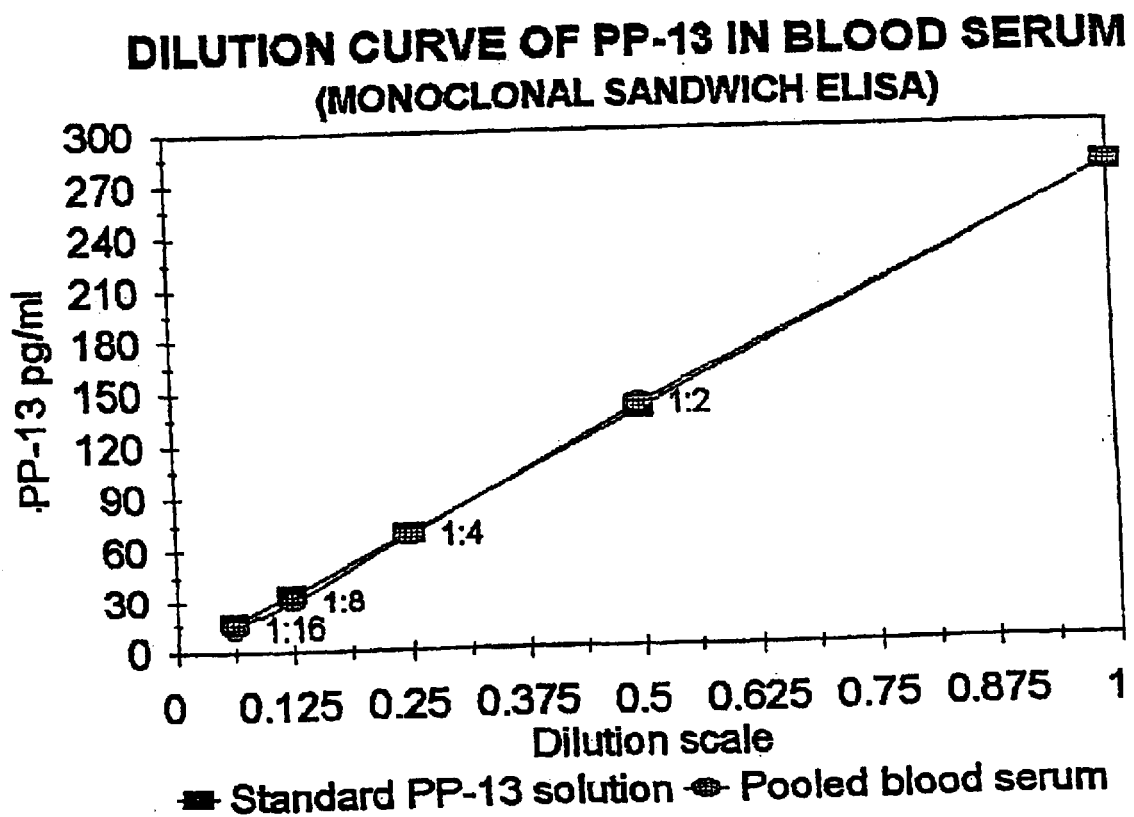
FIG. 14 illustrates a dilution curve of PP-13 in the blood serum (monoclonal sandwich ELISA)

The traditional method for detecting any type of non-specificity is an examination of parallelism between dilutions of specimen and standard. A high level of parallelism has been found between pooled blood serum samples and different concentrations of standard PP-13 solution in dilution experiment. Series of pooled serum dilutions has been made: 1:2, 1:4, 1:8 and 1:16. Normalized data points of blood serum and standard PP-13 solution were plotted (FIG. 14). Correlation between two dilution curves was calculated. The slope of pooled serum curve was=1.02; correlation coefficient r=0.9998; SD of residuals from the line=2.79; p value<0.0001 (two tailed).

(iv) Analytical Recovery Test

Figure 15:
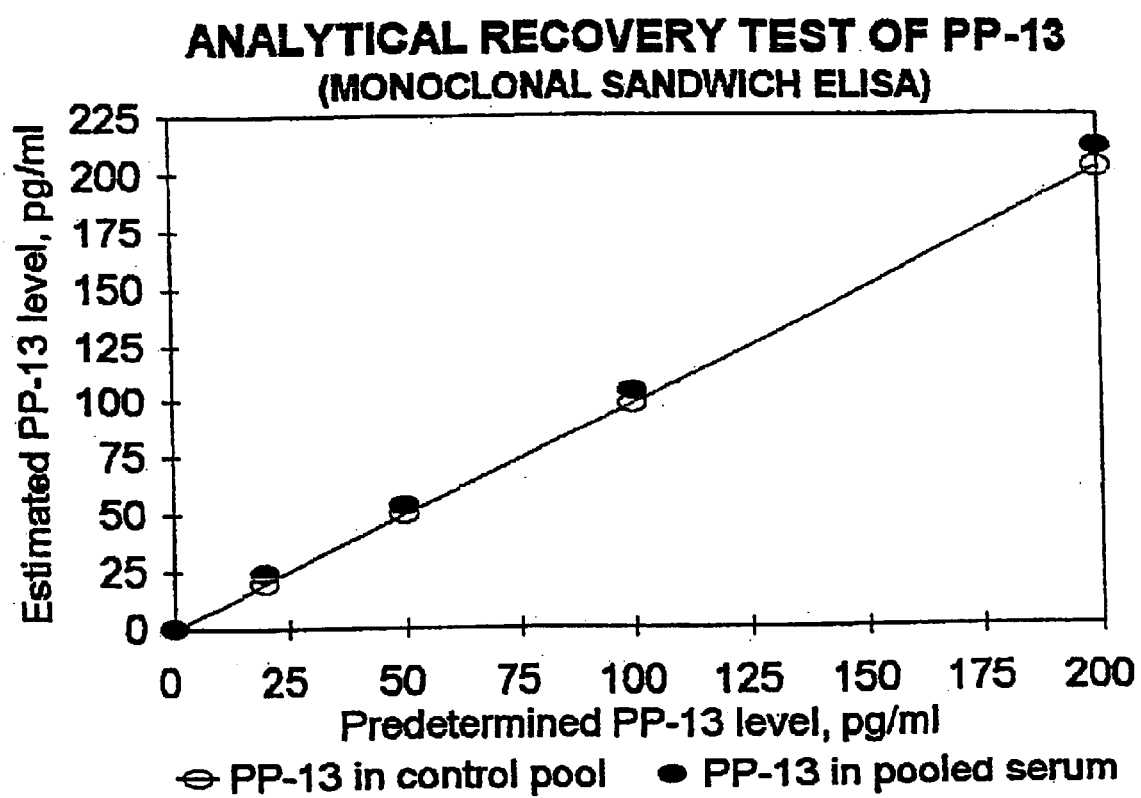
FIG. 15 illustrates an analytical recovery test of PP-13 (monoclonal sandwich ELISA).

This test is based on determination of known concentrations of PP-13 in a blood serum. Pooled blood serum from pregnant women was supplemented with four known amounts of PP-13: 20, 50, 100 and 200 pg/ml and analyzed together with the same concentrations of PP-13 control pool. The data points were plotted on a graph (FIG. 15). The overall analytical recovery was found to be 106.2% and the curve was linear with the slope=1.03. Correlation between estimated PP-13 levels in pooled blood serum and in the control pool was very strong (r=1).

(v) Intra- and Inter-assay Variation

These parameters were used for evaluation of an assay precision. Intra-assay variation was assessed as the coefficient of variation of control samples estimated within the same assay and calculated as:

$CV(\%)$=Standard deviation/mean*100%.

It was found to be between 1.5% and 3.5%. Inter-assay variation was calculated according to the same formula, based on estimations of aliquots from the quality-control pool in every assay run and was found to be between 2.6% and 8.4% (Table 1).

TABLE 1

Intra- and Inter-assay Variation of PP-13 ELISA

| PP-13 level pg/ml | Intra-assay variation (CV, %) (n = 16 each) | Inter-assay variation (CV, %) (n = 8 assays) |
| --- | --- | --- |
| 20 | 1.54 | 4.61 |
| 50 | 3.51 | 8.39 |
| 100 | 2.01 | 4.64 |
| 200 | 1.91 | 2.56 |

(c) PP-13 Levels in Human Blood Serum

Two-monoclonal antibody sandwich ELISA was employed for PP-13 measurement in blood serum of men, non-pregnant and pregnant women. It was found that PP-13 level in pregnant women was significantly higher (225.8+/−100.5 pg/ml) than detected concentrations in non-pregnant women (17.1+/−45.9 pg/ml) or in men (6.8+/−13.1 pg/ml). Many samples from men and non-pregnant women showed zero level of PP-13. These results suggest that PP-13 is a real placental protein and that two-antibody sandwich ELISA of PP-13 may be used as a screening tool in pregnant women.

References

1. Bohn. H., Winckler, W., Grundmann. U., Immunochemically detected placental proteins and their biological functions, *Arch. Gynecol. Obstet.*, 249:107–118 (1991).
2. Rutanen, E., Bohn, H., Seppala, M., Radioimmunoassay of placental protein 12: levels in amniotic fluid, cord blood, and serum of healthy adults, pregnant women and patients with trophoblastic disease. *Am. J. Obstet. Gynecol.*, 144:460–463 (1982).
3. Howell, R. J. S., Economides, D., Teisner, B., Farkas, A. G., Chard, T., Placental proteins 12 and 14 in pre-eclampsia, *Acta. Obstet. Gynecol., Scand.*, 68:237–240 (1989).
4. Scherbakova, L. A., Gocze, P. M., Olefirenko, G. A., Than, G. N., Szabo, D. G., Petrunin, D. D., Tatarinov, Yu, S., Csaba, I. F., Comparative study of enzyme-linked immunosorbent assay and radioinmunoassay techniques in determining serum placental protein 14 levels in gynecologic patients. *Tumor Biol.*, 12:267–271 (1991).
5. Giulian, G. G., Moss R. L., and Greaser, M., Improved Methodology for Analysis and Quantitation of Proteins and one-dimensional silver-stained gel. Anal. Biochem., 129:277–287 (1983).
6. Eshhar, Z., Blatt, C., Bergman, Y., Haimovich, J., Induction of secretion of IgM from cells of the B cell line 38C-13 by somatic cell hybridization. *J. Immunol.* 122:2430–2434 (1979).

What is claimed is:

1. A monoclonal IgG antibody (Mab) capable of binding Placental Protein 13 (PP-13) and of detecting PP-13 at a concentration of at least 10 pg/ml in a sandwich ELISA assay.

2. The Mab according to claim 1 produced by a hybridoma cell selected from the group consisting of clones deposited under accession nos. I-2134, I-2135, I-2136, I-2137, and I-2138.

3. The Mab according to claim 2 produced by the hybridoma clone deposited under accession no. I-2135 or I-2136.

4. A hybridoma selected from the group consisting of clones deposited under accession nos. I-2134, I-2135, I-2136, I-2137 and I-2138.

5. An immunoassay for measuring the level of PP-13 in a biological fluid, comprising the steps of:

(a) bringing said fluid into contact with a Mab according to any of claim 1, 2, or 3, thereby forming Mab-PP-13 complexes;

(b) exposing said complexes to a second Mab according to any of claim 1, 2, or 3 linked to a signal-generating molecule, said second Mab being capable of binding said complexes; and (c) providing conditions conducive to the production of a signal generated by said signal-generating molecule, the level of said signal indicating the level of PP-13 in the biological fluid, wherein said immunoassay is capable of measuring PP-13 at a concentration of 10 pg/ml.

6. The immunoassay according to claim 5, wherein said Mab in step (a) is bound to a solid phase.

7. The immunoassay according to claim 6, wherein said signal generating molecule is an enzyme.

8. The immunoassay according to claim 5, wherein said signal generating molecule is an enzyme.

9. The immunoassay according to claim 5, wherein said signal generating molecule is a ligand, and step (c) of claim 5 comprises incubating the product of step (b) with a ligand binding molecule linked to an enzyme.

10. A kit for measuring the level of PP-13 in a biological fluid, comprising:

(a) a Mab according to claim 1;

(b) a second antibody linked to a signal-generating molecule, wherein said second antibody is also a Mab according to claim 1; and (c) PP-13 standard solutions.

11. A kit for measuring the level of PP-13 in a biological fluid, comprising:

(a) a Mab according to any of claim 1, 2, or 3;

(b) a second Mab according to any of claim 1, 2, or 3 linked to a signal-generating molecule; and (c) PP-13 standard solutions.

12. The Mab according to claim 1, capable of detecting PP-13 at a concentration of 0.05 ng/ml in a sandwich ELISA assay.

13. The kit according to claim 10, wherein said signal generating molecule is an enzyme.

14. The kit according to claim 13, wherein said signal generating molecule is an enzyme.

15. The kit according to claim 13, wherein said signal generating molecule is a ligand, and said kit further comprises a ligand binding molecule linked to an enzyme.

16. The kit according to claim 15, wherein said ligand is biotin and said ligand-binding molecule is extravidin.

17. The kit according to claim 10, wherein said signal-generating molecule is biotin and the kit further comprises extravidin linked to an enzyme.

* * * * *

UNITED STATES PATENT AND TRADEMARK OFFICE
CERTIFICATE OF CORRECTION

PATENT NO. : 6,790,625 B1
DATED : September 14, 2004
INVENTOR(S) : Paltieli et al.

It is certified that error appears in the above-identified patent and that said Letters Patent is hereby corrected as shown below:

Column 10,
Lines 8 and 9, delete "claim" and insert therefor -- claims --;
Line 18, delete "claim 13" and insert therefor -- claim 11 --;
Line 20, delete "claim 13" and insert therefor -- claim 10 --.

Signed and Sealed this

Eleventh Day of October, 2005

JON W. DUDAS
*Director of the United States Patent and Trademark Office*